US007686019B2

(12) United States Patent
Weiss et al.

(10) Patent No.: US 7,686,019 B2
(45) Date of Patent: Mar. 30, 2010

(54) AUTO-INFLATION CUFFS (76) Inventors: Markus Weiss, Sunnewis 4, Bauma (CH) 8494; William T. Denman, 15 Hampshire St., Mansfield, MA (US) 01048

( * ) Notice: Subject to any disclaimer, the term of this patent is extended or adjusted under 35 U.S.C. 154(b) by 581 days.

(21) Appl. No.: 11/287,163

(22) Filed: Nov. 23, 2005

(65) Prior Publication Data
US 2007/0113857 A1    May 24, 2007

(51) Int. Cl.
*A61M 11/00* (2006.01)
(52) U.S. Cl. .............................. 128/207.15; 128/205.24
(58) Field of Classification Search ............ 128/201.13, 128/205.24, 207.15, 207.14, 207.18, 206.26, 128/200.24, 204.18
See application file for complete search history.

(56) References Cited
U.S. PATENT DOCUMENTS

| 3,205,890 | A | * | 9/1965 | Dritz | 128/207.15 |
|---|---|---|---|---|---|
| 3,565,079 | A | * | 2/1971 | Jackson | 128/207.15 |
| 3,642,005 | A | * | 2/1972 | McGinnis | 128/207.15 |
| 3,731,692 | A | * | 5/1973 | Goodyear | 128/207.15 |
| 4,471,775 | A | * | 9/1984 | Clair et al. | 128/205.24 |
| 4,825,862 | A |   | 5/1989 | Sato et al. |   |
| 4,856,510 | A |   | 8/1989 | Kowalewski | 128/207.15 |
| 5,060,647 | A | * | 10/1991 | Alessi | 128/207.14 |
| 5,218,970 | A | * | 6/1993 | Turnbull et al. | 600/561 |
| 5,235,973 | A |   | 8/1993 | Levinson |   |
| 5,291,882 | A | * | 3/1994 | Makhoul et al. | 128/207.14 |
| 5,471,058 | A | * | 11/1995 | Nakagawa et al. | 250/291 |
| 5,937,861 | A |   | 8/1999 | Augustine | 128/207.15 |
| 6,530,898 | B1 | * | 3/2003 | Nimkar et al. | 604/97.03 |
| 6,588,421 | B1 | * | 7/2003 | Diehl et al. | 128/201.13 |
| 6,647,984 | B1 | * | 11/2003 | O'Dea | 128/207.16 |
| 2004/0020491 | A1 | * | 2/2004 | Fortuna | 128/207.15 |

FOREIGN PATENT DOCUMENTS

DE    20 2005 002536 U1    5/2005
WO    WO 2005/009522 A     2/2005

OTHER PUBLICATIONS

D. Lugrin, et al., "Experimental and clinical study of a enw foam-filled cuff tube," *Review de Laryngologie*, vol. 110, No. 3, pp. 323-326, 1989.
Scott J. Greene, et al., "A Foam Cuff Endtracheal Tube T-Piece System for Use with Nitrous Oxide Anesthesia," *Anesthesia and Analgesia*, vol. 65, No. 12, pp. 1359-1360, 1986.

* cited by examiner

*Primary Examiner*—Steven O Douglas
(74) *Attorney, Agent, or Firm*—Fletcher Yoder (57) ABSTRACT

A medical ventilation device comprising a cannula having proximal and distal ends; an inflatable cuff adapted to be inflated to an inspiratory pressure, the cuff attached to and surrounding a portion of the cannula toward the distal end thereof; an inspiratory pressure inflation tube having first and second ends, the first end in communication with an interior of the inflatable cuff, the second end adapted to communicate with an inspiratory pressure source; and a pressure valve in communication with the inspiratory pressure inflation tube.

20 Claims, 7 Drawing Sheets

AUTO-INFLATION CUFFS

TECHNICAL FIELD

The present disclosure, according to one embodiment, relates to inflatable cuffs for medical applications, and more particularly, to the controlled inflation of cuffs, such as, for example, cuffs surrounding a portion of tubes used in respiratory care such as tracheostomy or endotracheal tubes. For the purposes of the present disclosure, tracheostomy and endotracheal tubes will be referred to collectively as "tracheal tubes," unless otherwise stated.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

Tracheal tubes may be inserted for a variety of reasons, including mechanical ventilation, bypass of an obstruction, removal of secretions, and easier ventilation due to less dead space. In some circumstances, it may be desirable to seal the outside of the tracheal tube to the inner tracheal lining, i.e., the tracheal mucosa. During mechanical ventilation, this may be particularly true, since a closed circuit may be desirable for a ventilator to force a given volume of air or oxygen under pressure into a subject's lungs. When a subject is not being mechanically ventilated, a seal may or may not be used. Whether a seal is used generally depends on whether there is a risk of aspiration. Therefore, sometimes a seal is used either to prevent aspiration or to create a closed circuit for mechanical ventilation.

Tracheal tubes typically follow a basic concept that utilizes a curved, "L" shaped tube which serves as an artificial passage for exchange of air between a subject and an air source, typically either atmospheric air or a mechanical respirator. The tube is often enveloped at its distal end by a small, inflatable cuff, also called a balloon, which is inflated with a gas, such as air, or in some cases a liquid. The cuff engages the internal lining of the trachea in its cross-section to prevent air insufflated by a respirator into a subject from escaping to the environment through the tracheostomy or the larynx and pharynx, thus enabling the air or gas mixture to reach the lower airways by bulk flow and the pulmonary alveoli by diffusion (also referred to as positive pressure ventilation). The cuff also may aid in supporting the tube inside the trachea and in substantially the same axis as the trachea (e.g., to prevent the tube's tip from contacting the tracheal wall), as well as protecting the airway from aspiration.

The cuffs are usually manually inflated with pressurized air from a syringe or a manometer through a small bore "pilot tube." The air is injected into the proximal end of the pilot tube, which usually is a thin piece of tubing for its proximal half and a small diameter channel molded into the wall or on the surface of the tracheal tube for its distal half. The pilot tube terminates at its distal end within the inflatable cuff of the tracheal tube. The pilot tube may have a one-way valve at its proximal end to maintain pressure within the system.

Experience has shown that the intracuff pressure is usually maintained at less than the arterial end-capillary pressure, which is typically about 25 cm $H_2O$. This is consistent with experimental data suggesting that the capillary perfusion pressure in the tracheal mucosa is in the range of 30-40 cm $H_2O$. Thus, a cuff pressure of 25 cm $H_2O$ normally allows some blood flow. However, the numbers noted above are not absolute. Cuff pressures of 25 cm $H_2O$ may be occasionally too high because perfusion pressures may be lower than expected due, for example, to low blood pressure. Therefore, the best approach is typically to use the lowest cuff pressure consistent with achieving a tracheal-cuff and mucosal seal that allows positive-pressure ventilation and prevents aspiration into the trachea.

Intracuff pressure may increase when an anesthetic is administered, for example, during surgery. The anesthetic gas nitrous oxide may diffuse through the cuff material and into the cuff. The volume of gas within the cuff can increase because of nitrous oxide diffusion. The pressure within the cuff then increases and, therefore, the pressure against the tissue of the tracheal wall is also increased. This slowly increasing cuff pressure may not be detected by the clinician.

SUMMARY

Therefore, there is a need for cuffed tubes that are more stable within a subject than currently available tubes, while minimizing pressures within the cuffs.

In general, the tracheal tubes of the present disclosure may comprise an auto-inflating cuff to sealingly engage the trachea of a subject. "Auto-inflation," as used herein, refers to inflation of a cuff through inspiratory pressure. The pressure within the auto-inflating cuff may be regulated, controlled, or adjusted through the use of an integrated or attached pressure valve, as well as by restricting the flow of air into and/or out of the cuff.

When placed in the trachea, the devices and systems according to specific example embodiments of the present disclosure may perform a variety of functions. For example, they may be useful in preserving or maintaining the airway of a subject while, among other things, preventing ischemia of the tracheal mucosa and/or preventing aspiration. Such devices and systems may be particularly useful, among other things, in pediatric subjects, where damage to the tracheal mucosa occurs more readily. Such devices and systems also may be particularly useful in applications, for example, that require long term intubation.

The devices and systems according to specific example embodiments of the present disclosure also may, among other things, reduce the occurrence of undesirable displacement during ventilation or movement of a subject, allow for stabilization of the cuff using lower intracuff pressures, and allow for smaller sized cuffs.

The present disclosure, according to a specific example embodiment, provides a medical ventilation device comprising a cannula having proximal and distal ends; an inflatable cuff adapted to be inflated to an inspiratory pressure, the cuff attached to and surrounding a portion of the cannula toward the distal end thereof; an inspiratory pressure inflation tube having first and second ends, the first end in communication with an interior of the inflatable cuff, the second end adapted to communicate with an inspiratory pressure source; and a pressure valve in communication with the inspiratory pressure inflation tube.

DRAWINGS

Some embodiments of the disclosure may be understood by referring, at least in part, to the following description and the accompanying drawings in which.

DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Referring now to the drawings, the details of specific example embodiments are schematically illustrated. Like elements in the drawings will be represented by like numbers, and similar elements will be represented by like numbers with a different lower case letter suffix.

Figure 1A:
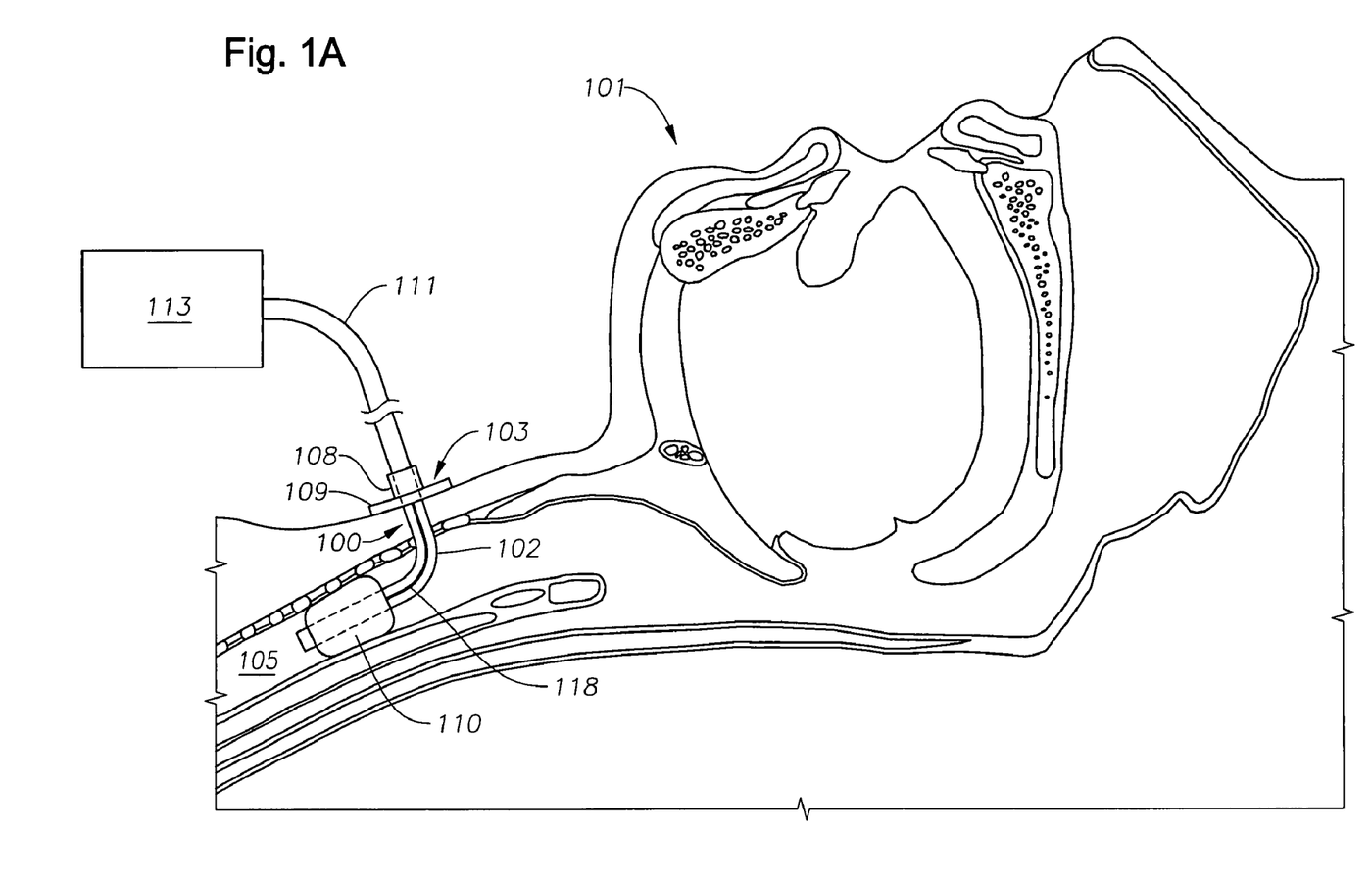
FIG. 1A is a schematic diagram of a ventilation system, according to a specific example embodiment of the present disclosure.

Referring to FIG. 1A, depicted is a schematic diagram of a ventilation system, according to a specific example embodiment of the present disclosure. A subject 101 has a stoma 103 (opening) leading to trachea 105 in which tracheal tube 100 is inserted. A flange 109 may be attached to subject's 101 neck, for example, by tape, straps, and the like (not shown). Integrally formed with flange 109, or proximate thereto, may be one or more of a pressure valve (not shown), a cuff connector site (not shown), a pilot balloon (not shown), and a tube (not shown). A ventilator hose 111 may couple a ventilator 113 to connector 108. A heat and moisture exchange ("HME") filter (not shown), which may include one or more ports and/or cuff connector sites, may be included between ventilator 113 and cannula 102, for example, integral with connector 108. An inflation cuff 110 may be proximate to the outer wall of cannula 102, and an inflation tube 118 may be within the outer wall of cannula 102 or proximate thereto.

Figure 1B:
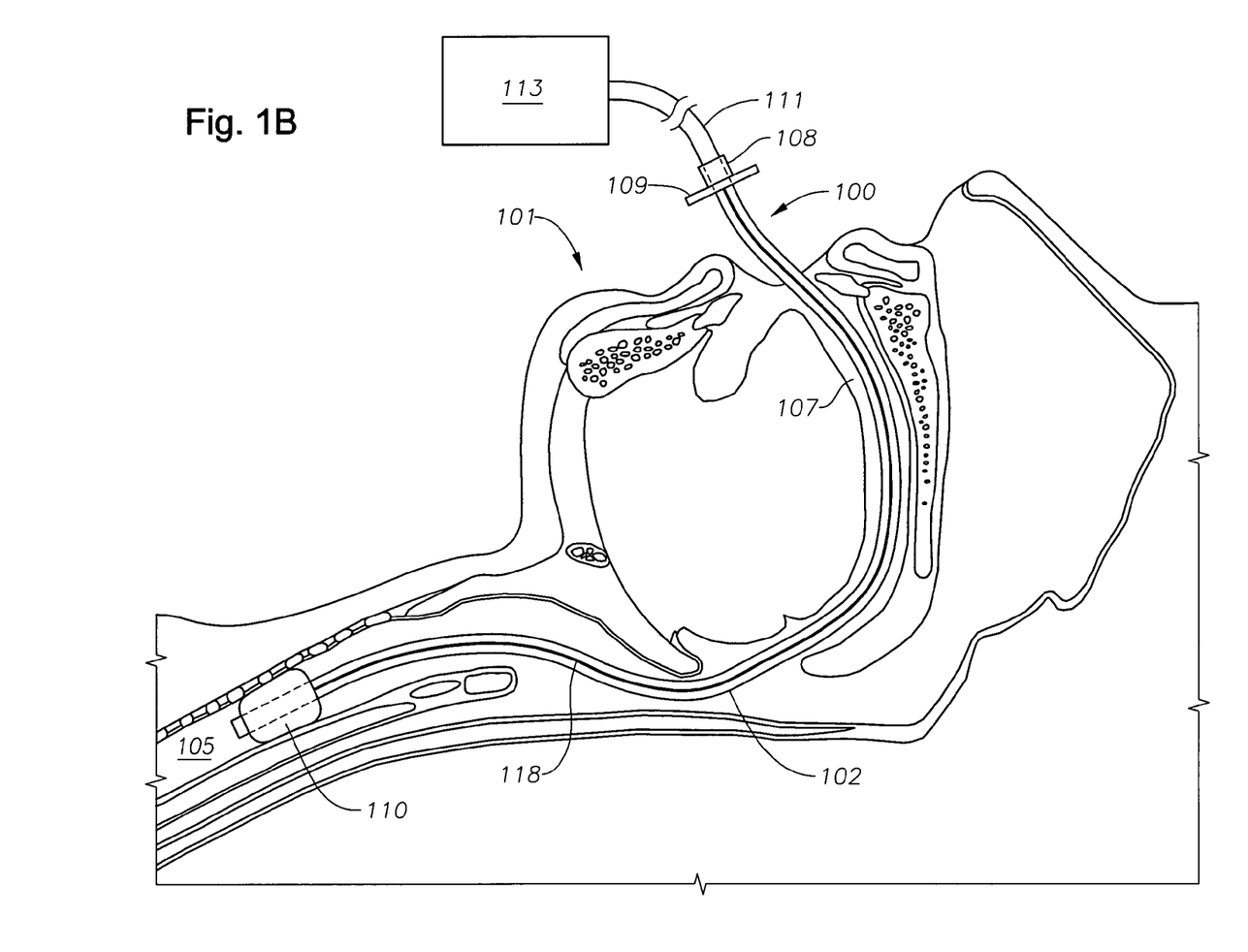
FIG. 1B is a schematic diagram of a ventilation system, according to another specific example embodiment of the present disclosure.

Referring to FIG. 1B, depicted is a schematic diagram of a ventilation system, according to a specific example embodiment of the present disclosure. Tracheal tube 100 is inserted through subject's 101 mouth 107 and into trachea 105. A ventilator hose 111 may couple a ventilator 113 to connector 108. Integrally formed with flange 109, or proximate thereto, may be one or more of a pressure valve (not shown), a cuff connector site (not shown), a pilot balloon (not shown), and a tube (not shown). A heat and moisture exchange ("HME") filter (not shown), which optionally may include one or more ports and/or cuff connector sites, may be included between ventilator 113 and cannula 102. An inflation cuff 110 may be proximate to the outer wall of cannula 102, and an inflation tube 118 may be within the outer wall of cannula 102 or proximate thereto.

Figure 2A:
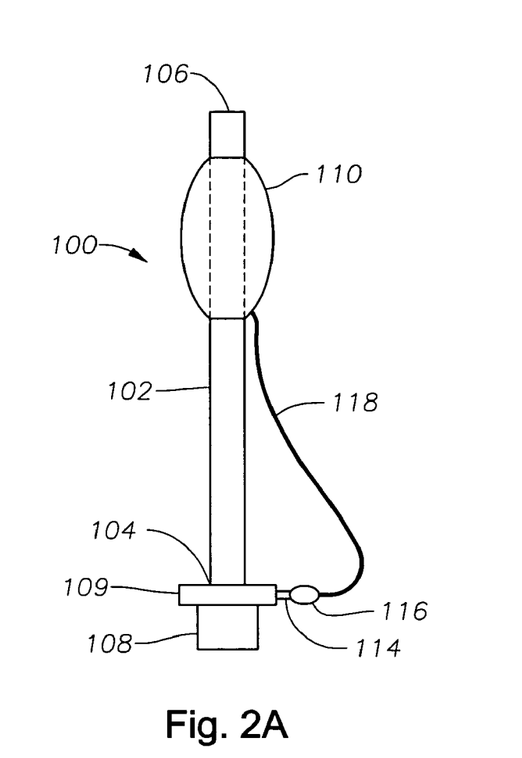
FIG. 2A is a schematic of a tracheal tube, according to a specific example embodiment of the present disclosure.
Figure 2B:
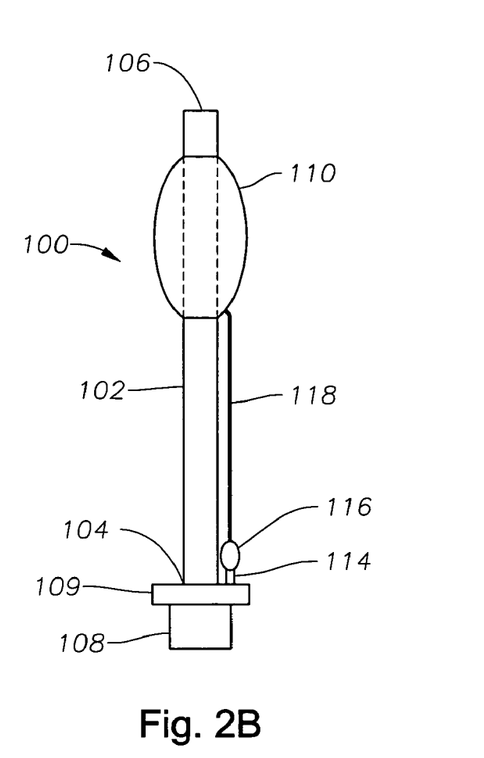
FIG. 2B is a schematic of a tracheal tube, according to another specific example embodiment of the present disclosure.

Referring to FIGS. 2A and 2B depicted are schematic diagrams of tracheal tubes, according to specific example embodiments of the present disclosure. Tracheal tube 100 may comprise cannula 102 having a proximal end 104 and a distal end 106. Cannula 102 may be sized to fit within the trachea of a subject, and may be formed, for example, from a length of flexible, tissue-compatible plastics, such as polyvinyl chloride or another plastic, silicon rubber, or another sufficiently flexible material. The proximal end 104 of cannula 102 may include connector 108 having flange 109. If desired, connector 108 may be used to connect tracheal tube 100 to a breathing apparatus or appropriate ventilator. Connector 108 may have standard sizes, among other things, to conveniently mate with commercially available breathing equipment. Tracheal tube 100 also may include an HME filter. Such an HME filter may be in communication with the lumen of cannula 102, for example, integral to connector 108 or attached to connector 108.

An inflatable cuff 110 sheathes cannula 102 at the distal end 106. Cuff 110 may be adapted to provide, when placed in a subject, an airway seal during positive-pressure ventilation, protection from aspiration, or both, without causing significant trauma to the trachea. Accordingly, cuff 110 may be formed so as to have a sufficiently large cuff volume to fill a gap between the outer wall of cannula 102 and the inner wall of a subject's trachea (not shown). Cuff 110 may comprise a flexible, inflatable, circumferential cuff or balloon. Cuff 110 may be formed from any biocompatible material. For example, cuff 110 may be formed from a thin film of plastic (e.g., polyurethane), rubber, or another flexible material. Cuff 110 may be formed from a material resistant to gas (e.g., nitrous oxide, oxygen) permeation, such as a crosslinked, polyester polyurethane resin, or cuff 110 may be formed from a material having a thickness which resists gas permeation; however, resistance to gas permeation may not be necessary, as cyclic inflation evacuates additional amounts of gases.

The cuff 110 may be inflated by means of inflation tube 118 extending along cannula 102. Tube 118 may be separate from cannula 102, or tube 118 may be integrally formed with the wall of cannula 102 (not shown). Tube 118 is in communication with the interior of cuff 110 for inflation and deflation thereof, and the other end of tube 118 may be in communication with both an inspiratory pressure source (e.g., a ventilator), as well as in communication with one or more of the internal lumen of cannula 102, cuff connector site 114, HME filter (not shown), T-Piece-adapter (not shown), and a pressure valve (not shown). The term pressure valve, as used herein, refers a device for one or more of controlling, regulating, adjusting, maintaining, and releasing intracuff pressure. Examples of pressure valves include, but are not limited to, pressure regulators, pressure release valves, adjustable valves, and air passageways configured to trap or restrict air flow to or from a cuff. Tube 118 may be adapted to receive pilot balloon 116. Alternatively, tube 118 may be integrally formed with pilot balloon 116, for example, by expanding tube 118 into a balloon shape having sufficient compliance. Pilot balloon 116 is in communication with cuff connector site 114, which may be located on flange 109 at the proximal end 104 of the tracheal tube 100. Cuff connector site 114 may be adapted to receive pilot balloon 116 and communicates with the lumen of connector 108, thereby providing a passageway to inflate cuff 110. Pilot balloon 116 and cuff connector site 114 may be disposed distally to flange 109 (e.g., axially to cannula 102) (shown in FIG. 2B). Such a configuration may place pilot balloon 116 and cuff connector site 114 within a subject. Alternatively, pilot balloon 116 and cuff connector site 114 may be disposed proximally to flange 109 (shown in FIG. 2A).

Tube 118 may be configured to decrease deflation of the cuff 110 during expiration, or to partially trap air in cuff 110. In this way, expansion of cuff 110 may be maintained during expiration while ensuring that the pressure within cuff 110 does not exceed the peak airway inflation pressure during inspiration. Suitable configurations include, but are not limited to, forming tube 118 to progressively expand distally, narrowing the inner diameter of tube 118, and providing an adjustable regulator or valve capable of restricting airflow through tube 118. Optionally, the upper inflation pressure may be regulated with a pressure release valve (not shown).

For fully deflating the cuff 110 (e.g., for extubation and/or air leak testing), the pilot balloon 116 may be disconnected from connector site 114 and manually deflated using, for example, a syringe connected to the pilot balloon 116. Alternatively, an additional port (not shown) for evacuating air from cuff 110 may be integral with connector 108, for example, at flange 109. When included, the port may be in communication with tube 118. The port also may be selectively openable and provide a means to access cuff 110, for example, to inflate or deflate cuff 110 and/or to equalize the pressure in cuff 110 to ambient pressure. The port may be adapted to receive a cap (not shown). The port also may be used for attachment of a monitoring device or regulator, for example, an electronic cuff pressure regulator (not shown) to, among other things, measure intracuff pressure. A separate positive pressure inflation valve (not shown), which may be adjustable or fixed, may be added to tracheal tube 100, for example, at the port or integral with the port.

In use, tracheal tube 100 may be placed into the windpipe through the mouth, through the nose, or through a tracheotomy, for example, to facilitate narcosis respiration or therapeutic respiration. Inspiratory pressure from a ventilator (not shown) provides air through tube 118 and into cuff 110. In this way, the inspiratory pressure may provide the means to inflate cuff 110 to sealingly engage tracheal tube 100 in the trachea of a subject. Such auto-inflation may allow, among other things, sealing of the trachea without the acute and sustained hyperinflation arising from syringe or manometer inflation. Auto-inflation of cuff 110 may allow the intracuff pressure to be equal to, or less than, the airway pressure in the trachea. In this regard, use of the tracheal tubes according to present disclosure may prevent damage to a subject's trachea, among other things, because cuff 110 may engage the trachea in proportion to the inspiratory pressure. In addition, insufflated gases that may diffuse into cuff 110 should not increase intracuff pressure, among other things, because with expiration, diffused gases are allowed to escape from cuff 110. Use of tracheal tube 100, as well as other tracheal tubes of the present disclosure, may free a clinician from monitoring cuff pressure, among other things, because upper inspiratory pressure may be noted from, for example, a ventilator.

Figure 3A:
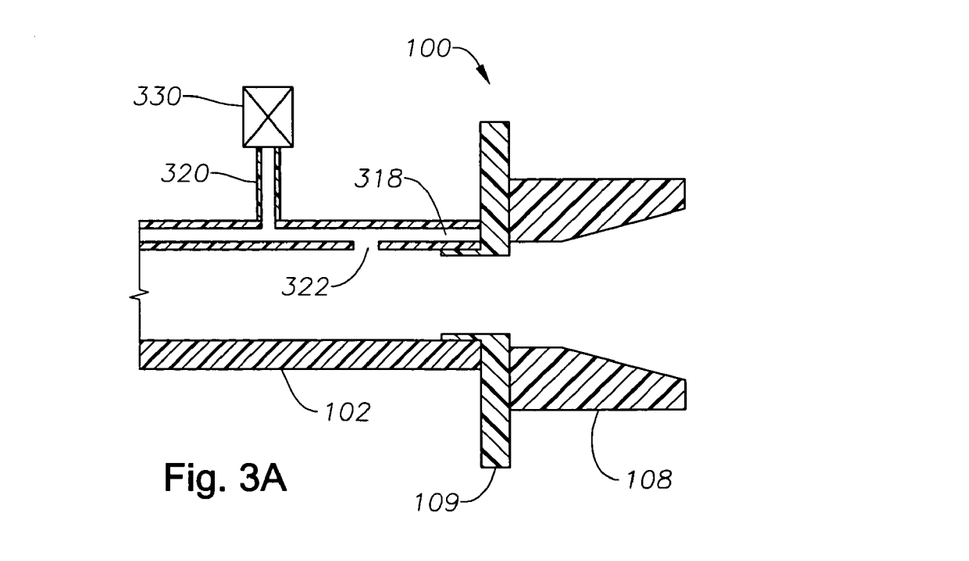
FIG. 3A is a cross-sectional schematic of a tracheal tube, according to another specific example embodiment of the present disclosure.

Referring to FIG. 3A, depicted is a cross-sectional schematic diagram of a portion of a tracheal tube 100, according to another specific example embodiment of the present invention. In this embodiment, cuff 110 (not shown) may be inflated by means of inflation tube 318 extending along and integrally formed with cannula 102. Tube 318 is in communication with the interior of cuff 110 (not shown) for inflation and deflation thereof, and the other end of tube 318 is in communication with the lumen of cannula 102 via opening 322, thereby providing a passageway to inflate cuff 110. Port 320 may be attached to the wall of cannula 102 and is in communication with tube 318. Port 320 may be selectively openable and provide a means to access cuff 110, for example, to inflate or deflate cuff 110 or to equalize the pressure in cuff 110 to ambient pressure. Port 320 may be adapted to receive a cap (not shown) and a pressure valve 330 (e.g., a pressure release valve). Pressure valve 330 may be adjustable or fixed. Such a pressure valve, among other things, may help prevent excessive intracuff pressure during intermittent positive pressure ventilation ("IPPV"). Tracheal tube 100 also may include an HME filter (not shown). Such an HME filter may be in communication with the lumen of cannula 102, for example, integral to connector 108 or attached to connector 108.

Figure 3B:
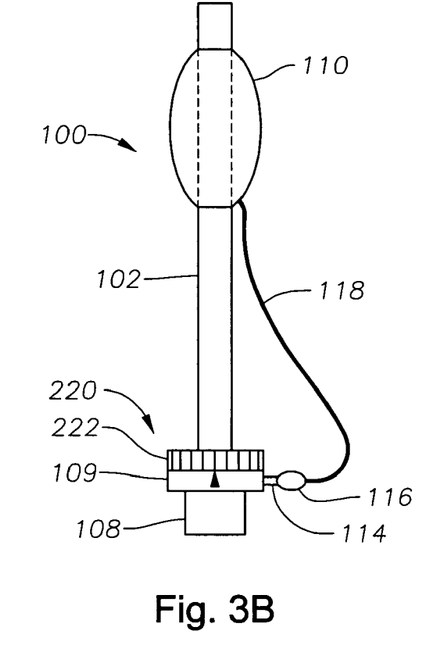
FIG. 3B is a schematic of a tracheal tube, according to another specific example embodiment of the present disclosure.
Figure 3C:
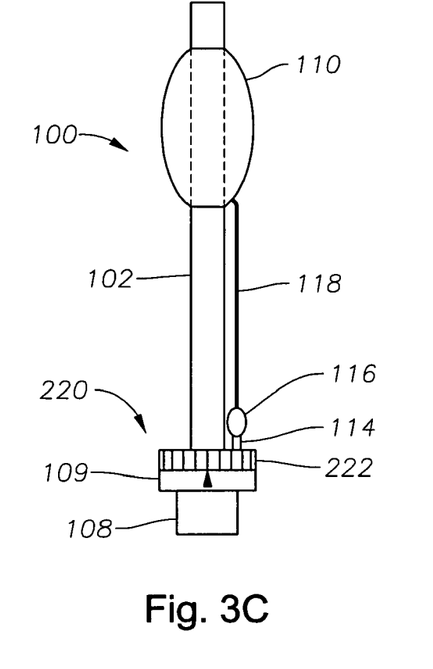
FIG. 3C is a schematic of a tracheal tube, according to another specific example embodiment of the present disclosure.

Referring to FIG. 3B and FIG. 3C, depicted are schematic diagrams of tracheal tubes 100, according to other specific example embodiments of the present disclosure. In these embodiments, an adjustable pressure valve 220 may be positioned distally to connector 108 or integral to connector 108 (not shown), and be in communication with the lumen of cannula 102 and cuff connector site 114. In this way, adjustable pressure valve 220 may be placed so as to affect the pathway of air to cuff 110. Examples of adjustable pressure valves include, but are not limited to, pressure regulators, pressure release valves, adjustable valves, and air passageways configured to trap or restrict air flow to or from a cuff. Such a pressure valve may help ensure that sufficient intracuff pressure is provided to cuff 110 and/or maintained in cuff 110 during IPPV, as well as during spontaneous ventilation, such that cuff 110 remains substantially sealingly engaged to the trachea. The use of a pressure valve may substantially minimize any air leakage from the higher tracheal airway pressure as compared to ambient pressure at the positive-end expiratory pressure ("PEEP") values that occur during expiration. In one aspect, adjustable pressure valve 220 may also act as a positive pressure inflation valve, among other things, to limit the upper intracuff pressure during inspiration (peak inspiratory pressure, "PIP"). In another aspect, a separate positive pressure inflation valve (not shown), which may be adjustable or fixed, may be added to tracheal tube 100, for example, at connector site 114 or integral with connector site 114. Adjustable pressure valve 220 may be adjusted in a range from about a value corresponding to approximately the PEEP to about a value corresponding to approximately the PIP. Adjustment of pressure valve 220 may be achieved, for example, by turning adjustment ring 222 having, for example, an adjustable orifice (not shown). Tracheal tube 100 also may include an HME filter (not shown). Such an HME filter may be in communication with the lumen of cannula 102, for example, integral to connector 108 or attached to connector 108.

For fully deflating cuff 110 (e.g., for extubation), the pilot balloon 116 may be disconnected from connector site 114 and manually deflated using, for example, a syringe connected to the pilot balloon 116. Alternatively, an additional port (not shown) for evacuating air from cuff 110 may be integral with pressure valve 220 or flange 109. In this regard, air may be evacuated positioning adjustment ring 222 to allow evacuation through the port using, for example, a syringe or ambient pressure. When included, the port may be in communication with tube 118. The port also may be selectively openable and provide a means to access cuff 110, for example, to inflate or deflate cuff 110 or to equalize the pressure in cuff 110 to ambient pressure. The port may be adapted to receive a cap (not shown). The port also may be used for attachment of a monitoring device or regulator, for example, an electronic cuff pressure regulator (not shown) to, among other things, measure intracuff pressure. A separate positive pressure inflation valve (not shown), which may be adjustable or fixed, may be added to tracheal tube 100, for example, at the port or integral with the port.

Figure 3D:
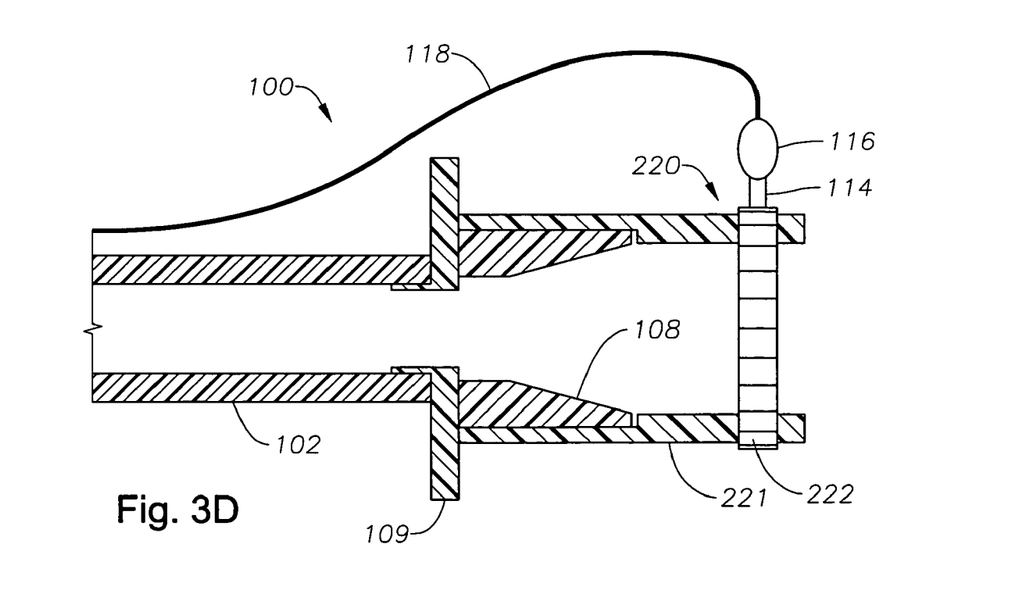
FIG. 3D is a schematic of a tracheal tube, according to another specific example embodiment of the present disclosure.

Referring to FIG. 3D, depicted is a schematic diagram of a portion of a tracheal tube 100, according to another specific example embodiment of the present invention. In this embodiment, cuff 110 (not shown) may be inflated by means of inflation tube 118 extending along cannula 102. Tube 118 is in communication with the interior of cuff 110 (not shown) for inflation and deflation thereof, and the other end of tube 118 is in communication with the internal lumen of an interposed T-piece 221 via pilot balloon 116 and connector site 114, thereby providing a passageway to inflate cuff 110. The T-piece 221 is interposed between connector 108 and respirator circuit tube (not shown). Adjustable pressure valve 220 may be integral to T-piece 221 and be in communication with the lumen of the T-piece and cuff connector site 114. In this way, adjustable pressure valve 220 may be placed so as to affect the pathway of air to cuff 110. Adjustable pressure valve 220 includes connector site 114 and adjustment ring 222. The cuff connector site 114 on pressure valve 220 may be adapted to receive a pilot balloon 116 and a cap (not shown). Pilot balloon 116 may be adapted to receive tube 118. Alternatively, tube 118 may be integrally formed with pilot balloon 116, for example, by expanding tube 118 into a balloon shape having sufficient compliance. T-piece 221 also may include an HME filter (not shown).

Adjustable pressure valve 220 may help ensure that sufficient intracuff pressure is provided to cuff 110 and/or maintained in cuff 110 during IPPV, as well as during spontaneous ventilation, such that cuff 110 remains substantially sealingly engaged to the trachea. The use of a pressure valve may substantially minimize any air leakage from the higher tracheal airway pressure as compared to ambient pressure at the PEEP values that occur during expiration. In one aspect, adjustable pressure valve 220 may also act as a positive-pressure inflation valve, among other things, to limit the upper intracuff pressure during inspiration. Adjustment of adjustable pressure valve 220 may be achieved by positioning adjustment ring 222 having, for example, an adjustable orifice (not shown).

Figure 3E:
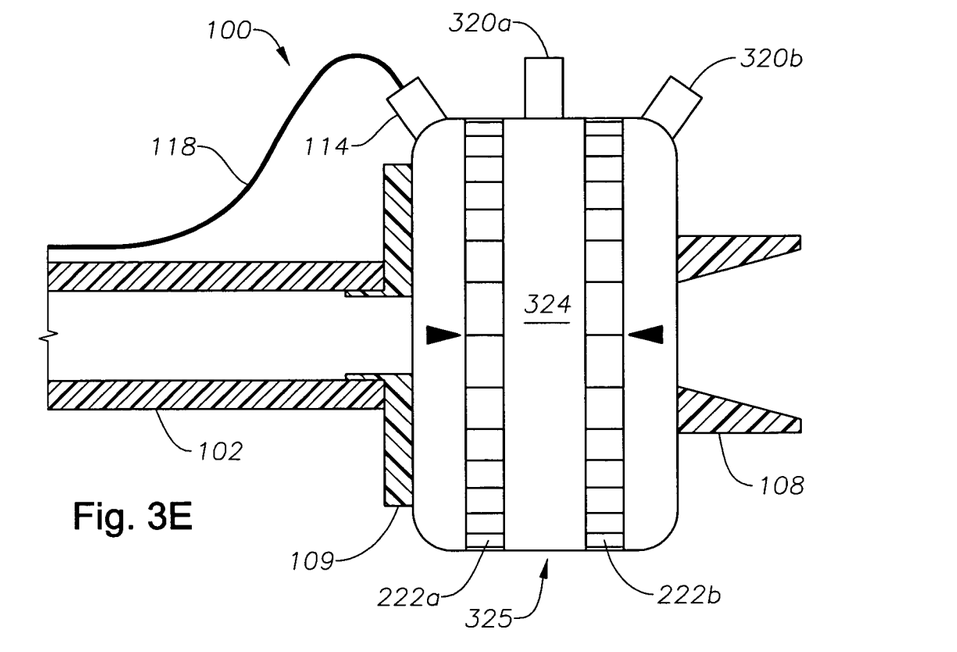
FIG. 3E is a schematic of a tracheal tube, according to another specific example embodiment of the present disclosure.

Referring to FIG. 3E, depicted is a schematic diagram of a portion of a tracheal tube 100, according to another specific example embodiment of the present invention. In this embodiment, cuff 110 (not shown) may be inflated by means of inflation tube 118 extending along cannula 102. Tube 118 is in communication with the interior of cuff 110 (not shown) for inflation and deflation thereof, and the other end of tube 118 is in communication with the lumen of HME filter 325, thereby providing a passageway to inflate cuff 110. Adjustable pressure valve 324 may be integral of the HME filter 325, and be in communication with it's lumen and cuff connector site 114. In this way, adjustable pressure valve 324 may be placed so as to affect the pathway of air to cuff 110. Adjustable pressure valve 324 includes connector site 114, port 320*a* and 320*b*, and adjustment ring 222*a* and 222*b*. Cuff connector site 114 may be adapted to receive tube 118, a pilot balloon (not shown), and a cap (not shown). Port 320*a* and 320*b* may be adapted to receive a cap (not shown) and a pressure valve (not shown), for example, a pressure release valve. Port 320*a* may be selectively openable, for example, by positioning adjustment ring 222*a* and/or 222*b* to allow access to cuff 110 for, among other things, evacuation of the cuff through the port using, for example, a syringe or ambient pressure. Port 320*b* may be used for attachment of a monitoring device, for example, an anesthesia gas monitoring unit (not shown).

Adjustable pressure valve 324 may help ensure that sufficient intracuff pressure is provided to cuff 110 during IPPV, as well as during spontaneous ventilation, such that cuff 110 remains substantially sealingly engaged to the trachea. The use of adjustable pressure valve 324 may minimize any air leakage from the higher tracheal airway pressure as compared to ambient pressure at the PEEP values that occur during expiration, as well as limit the upper PIP. Adjustable pressure valve 324 may be capable of separately adjusting the pressure inside cuff 110 during expiration and inspiration. Both adjustments may be made in a range from about a value corresponding to approximately the PEEP to about a value corresponding to approximately the PIP. Adjustment of adjustable pressure valve 324 may be achieved by positioning adjustment ring 222*a* and 222*b*, each of which may correspond to adjustment of either the inspiratory pressure or the expiratory pressure. Adjustment of pressure valve 324 may be achieved, for example, by turning adjustment ring 222*a* and 222*b* having, for example, an adjustable orifice (not shown).

Figure 4A:
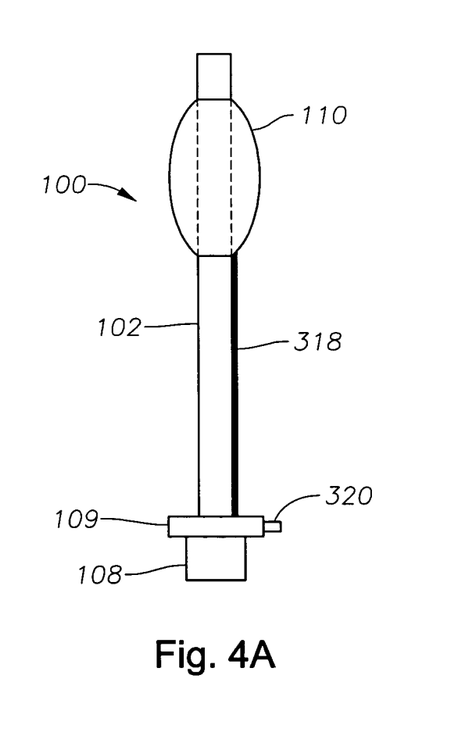
FIG. 4A is a schematic of a tracheal tube, according to another specific example embodiment of the present disclosure.

Referring to FIG. 4A, depicted is a schematic diagram of a tracheal tube, according to another specific example embodiment of the present disclosure. In this embodiment, cuff 110 may be inflated by means of inflation tube 318 extending along cannula 102. Tube 318 may be separate from cannula 102 (not shown), or tube 318 may be integrally formed with cannula 102. Tube 318 is in communication with the interior of cuff 110 for inflation and deflation thereof, and the other end of tube 318 is in communication with connector 108, thereby providing a passageway to inflate cuff 110. Port 320 may be attached to connector 108 and is in communication with tube 318. Port 320 may be selectively openable and provide a means to access cuff 110, for example, to inflate or deflate cuff 110 or to equalize the pressure in cuff 110 to ambient pressure. Port 320 may be adapted to receive a cap (not shown). Port 320 also may be used for attachment of a monitoring device or regulator, for example, an electronic or mechanical cuff pressure regulator (not shown) to, among other things, measure intracuff pressure. A separate positive pressure inflation valve (not shown), which may be adjustable or fixed, may be added to tracheal tube 100, for example, at port 320 or integral with port 320. Tracheal tube 100 also may include an HME filter (not shown). Such an HME filter may be in communication with the lumen of cannula 102, for example, integral to connector 108 or attached to connector 108.

Figure 4B:
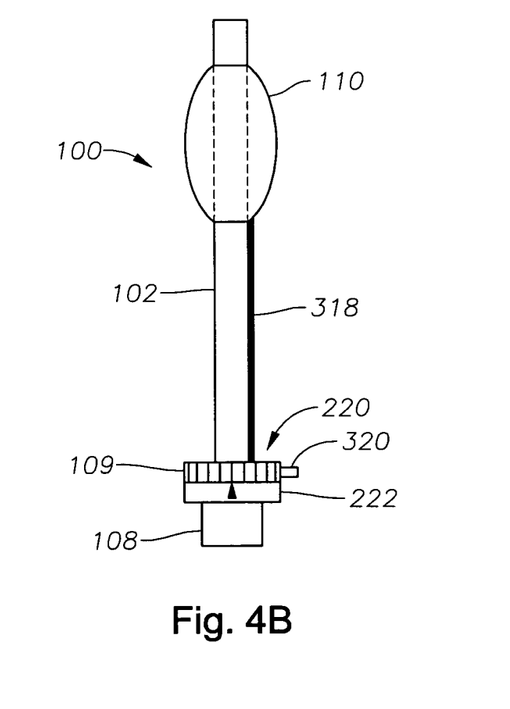
FIG. 4B is a schematic of a tracheal tube, according to another specific example embodiment of the present disclosure.

Referring to FIG. 4B, depicted is a schematic diagram of a tracheal tube, according to another specific example embodiment of the present disclosure. In this embodiment, an adjustable pressure valve 220 may be positioned distally to connector 108, or integral to connector 108 (not shown), and in communication with cannula 102 and port 320. In this way, adjustable pressure valve 220 may be placed so as to affect the pathway of air to cuff 110. Such a pressure valve may help ensure that sufficient intracuff pressure is provided to cuff 110 and/or maintained in cuff 110 during IPPV, as well as during spontaneous ventilation, such that cuff 110 remains substantially sealingly engaged to the trachea. The use of a pressure valve may substantially minimize any air leakage from the higher tracheal airway pressure as compared to ambient pressure at the PEEP values that occur during expiration. In one aspect, adjustable pressure valve 220 may also act as a positive-pressure inflation valve, among other things, to limit the upper intracuff pressure during inspiration. In another aspect, a separate positive pressure inflation valve (not shown), which may be adjustable or fixed, may be added to tracheal tube 100, for example, at port 320 or integral with port 320. Adjustable pressure valve 220 may be adjusted in a range from about a value corresponding to approximately the PEEP to about a value corresponding to approximately the PIP. In addition, adjustable pressure valve 220 may be adjusted to help regulate, prevent, or allow air flow between tube 318 and port 320. Adjustment of pressure valve 220 may be achieved, for example, by turning adjustment ring 222. Tracheal tube 100 also may include an HME filter (not shown). Such an HME filter may be in communication with the lumen of cannula 102, for example, integral to connector 108 or attached to connector 108.

Figure 4C:
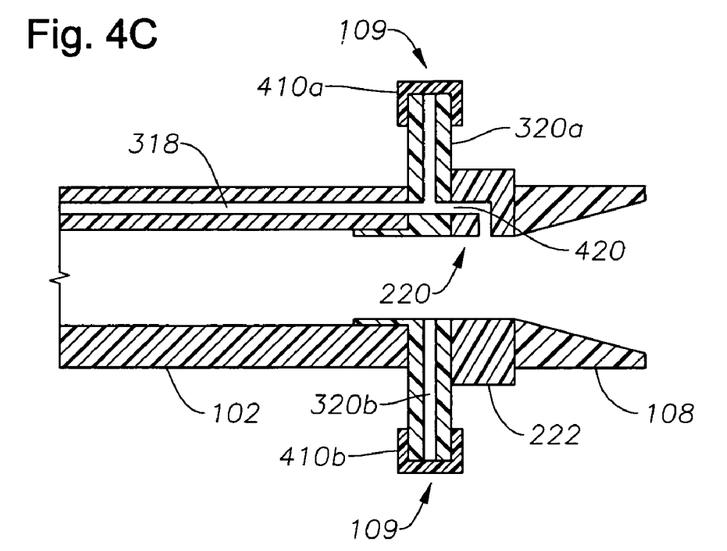
FIG. 4C is a cross-sectional schematic of a tracheal tube, according to another specific example embodiment of the present disclosure.

Referring to FIG. 4C, depicted is a cross-sectional schematic diagram of a tracheal tube 100, according to another specific example embodiment of the present disclosure. In this embodiment, cuff 110 (not shown) may be inflated by means of inflation tube 318 extending along cannula 102. Tube 318 may be separate from cannula 102 (not shown), or tube 318 may be integrally formed with cannula 102. Tube 318 is in communication with the interior of cuff 110 for inflation and deflation thereof, and the other end of tube 318 is in communication with connector 108, thereby providing a passageway to inflate cuff 110. Port 320a and 320b may be integral with flange 109, or they may be separate from flange 109 (not shown). Port 320a may be attached to connector 108 and is in communication with tube 318. Port 320a may be selectively openable and provide a means to access cuff 110, for example, to inflate or deflate cuff 110 or to equalize the pressure in cuff 110 to ambient pressure. Optionally, a pressure valve (not shown), for example, a fixed or adjustable pressure release valve, may be attached to port 320a. Port 320a and Port 320b may be adapted to receive cap 410a and 410b, respectively. Port 320a may be used for attachment of a monitoring device or regulator, for example, an electronic cuff pressure regulator (not shown) to, among other things, measure intracuff pressure. Port 320b also may be used for attachment of a monitoring device, for example, an anesthesia gas monitoring unit (not shown) to, among other things, monitor end-tidal $CO_2$. Tracheal tube 100 also may include an HME filter (not shown). Such an HME filter may be in communication with the lumen of cannula 102, for example, integral to connector 108 or attached to connector 108.

An adjustable pressure valve 220 may be positioned distally to connector 108 (not shown), or integral to connector 108, and in communication with cannula 102 and port 320a. In this way, adjustable pressure valve 220 may be placed so as to affect the pathway of air to cuff 110. In one aspect, adjustable pressure valve 220 may also act as a positive-pressure inflation valve, among other things, to limit the upper intracuff pressure during inspiration. In another aspect, a separate positive pressure inflation valve (not shown), which may be adjustable or fixed, may be added to tracheal tube 100, for example, at port 320a or integral with port 320a. Adjustable pressure valve 220 may be adjusted in a range from about a value corresponding to approximately the PEEP to about a value corresponding to approximately the PIP. In addition, adjustable pressure valve 220 may be adjusted to help regulate, prevent, or allow air flow between tube 318 and port 320a. Adjustment of pressure valve 220 may be achieved, for example, by turning adjustment ring 222 having, for example, an adjustable orifice 420. For fully deflating cuff 110 (e.g., for extubation), the adjustment ring 222 may be positioned to close orifice 420 and a syringe, for example, may be affixed to port 320a to manually deflated cuff 110.

Figure 4D:
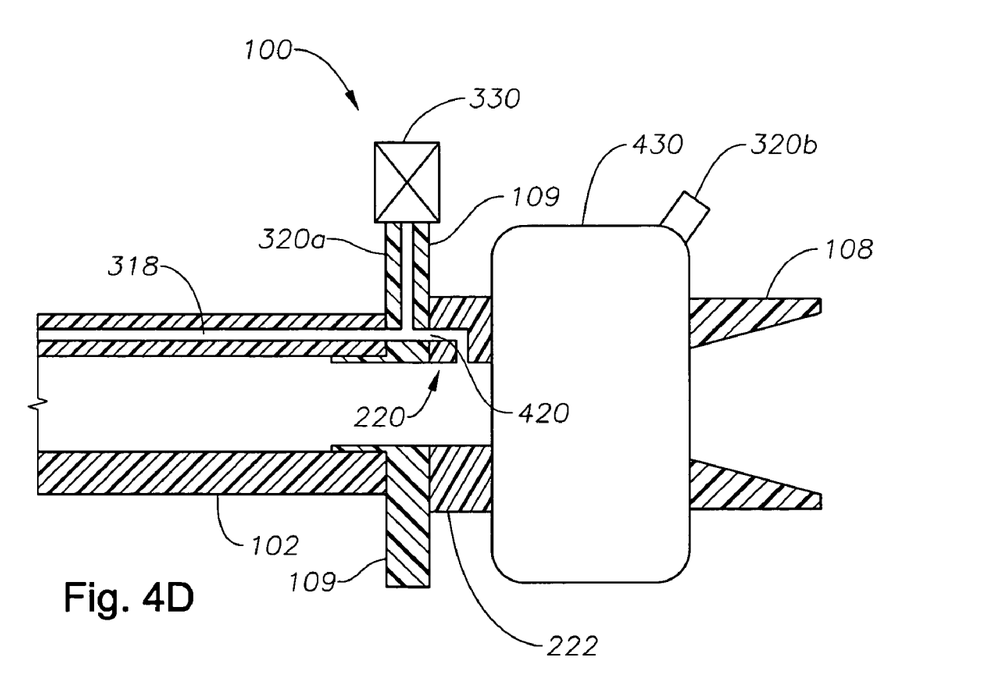
FIG. 4D is a schematic of a tracheal tube, according to another specific example embodiment of the present disclosure.

Referring to FIG. 4D, depicted is a schematic diagram of a tracheal tube 100, according to another specific example embodiment of the present disclosure. In this embodiment, cuff 110 (not shown) may be inflated by means of inflation tube 318 extending along cannula 102. Tube 318 may be separate from cannula 102 (not shown), or tube 318 may be integrally formed with cannula 102. Tube 318 is in communication with the interior of cuff 110 for inflation and deflation thereof, and the other end of tube 318 is in communication with connector 108, thereby providing a passageway to inflate cuff 110. Port 320a may be integral with flange 109, or separate from flange 109 (not shown). Port 320a may be attached to cannula 102 and is in communication with tube 318. Port 320a may be selectively openable and provide a means to access cuff 110, for example, to inflate or deflate cuff 110 or to equalize the pressure in cuff 110 to ambient pressure. Optionally, a pressure release valve 330, which may be fixed or adjustable, may be attached to port 320a. In another aspect, a separate positive pressure inflation valve (not shown), which may be adjustable or fixed, may be added to tracheal tube 100, for example, at port 320a or integral with port 320a. Port 320a may be adapted to receive a cap (not shown). Port 320a may be used for attachment of a monitoring device or regulator, for example, an electronic cuff pressure regulator (not shown). Integral with connector 108 is HME filter 430 in communication with the lumen of cannula 102. Port 320b on HME filter 430 may be selectably openable and used for, among other things, attachment of a monitoring device (not shown).

An adjustable pressure valve 220 may be positioned distally to cannula 102, and in communication with cannula 102 and port 320a. In this way, adjustable pressure valve 220 may be placed so as to affect the pathway of air to cuff 110. In one aspect, adjustable pressure valve 220 may also act as a positive-pressure inflation valve, among other things, to limit the upper intracuff pressure during inspiration. Adjustable pressure valve 220 may be adjusted in a range from about a value corresponding to approximately the PEEP to about a value corresponding to approximately the PIP. In addition, adjustable pressure valve 220 may be adjusted to help regulate, prevent, or allow air flow between tube 318 and port 320a. Adjustment of pressure valve 220 may be achieved, for example, by turning adjustment ring 222 having, for example, an adjustable orifice 420. For fully deflating cuff 110 (e.g., for extubation), the adjustment ring 222 may be positioned to close orifice 420 and a syringe, for example, may be affixed to port 320a to manually deflated cuff 110.

Figure 5:
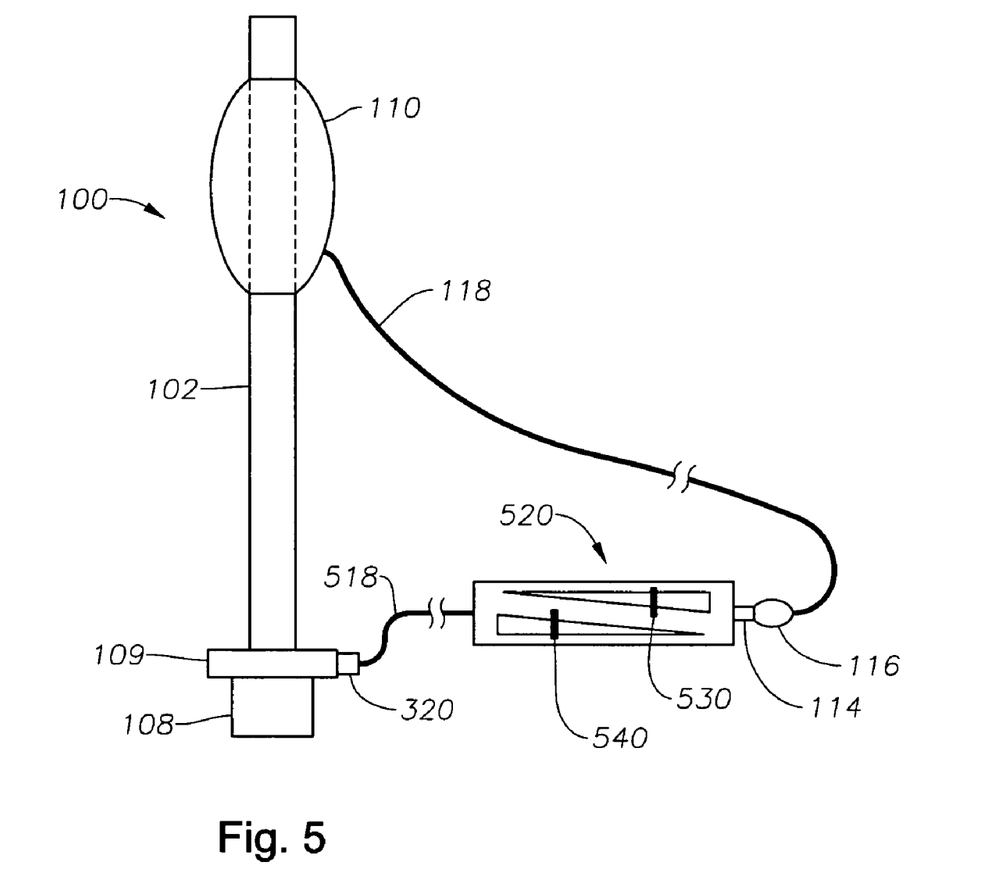
FIG. 5 is a schematic of a tracheal tube, according to another specific example embodiment of the present disclosure.

Referring to FIG. 5, depicted is a schematic diagram of a tracheal tube, according to another specific example embodiment of the present disclosure. In this embodiment, cuff 110 may be inflated by passageway for air formed by one or more of tube 118, pilot balloon 116, cuff connector site 114, adjustable regulator 520, regulator tube 518, and port 320. Tube 118 may be separate from cannula 102, or tube 118 may be integrally formed with the wall of cannula 102 (not shown). Tube 118 is in communication with the interior of cuff 110 for inflation and deflation thereof, and the other end of tube 118 may be adapted to receive pilot balloon 116. Alternatively, tube 118 may be integrally formed with pilot balloon 116, for example, by expanding tube 118 into a balloon shape having sufficient compliance. Pilot balloon 116 may be in communication with cuff connector site 114, which may be located on adjustable regulator 520. Cuff connector site 114 may be adapted to receive pilot balloon 116 and may communicate with adjustable regulator 520. Tracheal tube 100 also may include an HME filter (not shown). Such an HME filter may be in communication with the lumen of cannula 102, for example, integral to connector 108 or attached to connector 108.

Adjustable regulator 520 may also communicate with regulator tube 518, and regulator tube 518 may communicate with port 320. In this way, adjustable regulator 520 may be placed so as to affect the pathway of air to cuff 110. Port 320 may be attached to connector 108 and be in communication with an air supply (not shown). Port 320 may be selectively openable and provide access to cuff 110, for example, to inflate or deflate cuff 110. Port 320 may also be used for attachment of a monitoring device or regulator, for example, an electronic or mechanical cuff pressure regulator.

Adjustable regulator 520 may help ensure that sufficient intracuff pressure is provided to cuff 110 during IPPV, as well as during spontaneous ventilation, such that cuff 110 remains substantially sealingly engaged to the trachea. The use of a regulator may minimize any air leakage from the higher tracheal airway pressure as compared to ambient pressure at the PEEP values that occur during expiration, as well as limit the upper PIP. Adjustable regulator 520 may be capable of separately adjusting the pressure inside cuff 110 during expiration and inspiration. Both adjustments may be made in a range from about a value corresponding to approximately the PEEP to about a value corresponding to approximately the PIP. Adjustment of adjustable regulator 520 may be achieved by positioning inspiration controller 530 and expiration controller 540.

While embodiments of this disclosure have been depicted, described, and are defined by reference to example embodiments of the disclosure, such references do not imply a limitation on the disclosure, and no such limitation is to be inferred. The subject matter disclosed is capable of considerable modification, alteration, and equivalents in form and function, as will occur to those ordinarily skilled in the pertinent art and having the benefit of this disclosure. The depicted and described embodiments of this disclosure are examples only, and are not exhaustive of the scope of the disclosure.

What is claimed is:

1. A medical ventilation device comprising:
    a cannula having proximal and distal ends, wherein the cannula is in fluid communication with an inspiratory pressure source adapted to provide respiratory gases to a patient at an inspiratory pressure;
    an inflatable cuff adapted to be inflated to the inspiratory pressure, the cuff attached to and surrounding a portion of the cannula toward the distal end thereof;
    an inspiratory pressure inflation tube having first and second ends, the first end in communication with an interior of the inflatable cuff, the second end adapted to communicate with the inspiratory pressure source and a cuff pressure monitoring device; and
    a pressure valve in communication with the inspiratory pressure inflation tube.

2. The medical ventilation device according to claim 1, wherein the inspiratory pressure source comprises a ventilator.

3. The medical ventilation device according to claim 1, wherein the inflation tube is integrally formed with the cannula.

4. The medical ventilation device according to claim 1, further comprising a pilot balloon proximate to the inflation tube.

5. The medical ventilation device according to claim 1, wherein the inflation tube is configured to at least partially trap air in the inflatable cuff.

6. The medical ventilation device according to claim 1, wherein the pressure valve is adjustable.

7. The medical ventilation device according to claim 1, wherein the pressure valve comprises a pressure release valve capable of affecting the pathway of air in the inspiratory pressure inflation tube.

8. The medical ventilation device according to claim 1, wherein the pressure valve comprises a positive pressure inflation valve.

9. The medical ventilation device according to claim 1, wherein the pressure valve is capable of adjustment in a range from about a value corresponding to the positive-end expiratory pressure to about a value corresponding to the peak inspirational pressure.

10. The medical ventilation device according to claim 1, wherein the pressure valve comprises an adjustable regulator.

11. The medical ventilation device according to claim 1, wherein the pressure valve comprises an adjustable regulator that is capable of separately adjusting the pressure inside the cuff during expiration and inspiration.

12. The medical ventilation device according to claim 1, wherein the pressure valve comprises an adjustable regulator that is capable of separately adjusting a pressure inside the cuff during expiration and inspiration, and wherein the pressure is capable of adjustment in a range from about a value corresponding to the positive-end expiratory pressure to about a value corresponding to the peak inspiratory pressure.

13. The medical ventilation device according to claim 1, further comprising a port, wherein the port is selectively openable to provide access to the inflation tube.

14. The medical ventilation device according to claim 1, further comprising a first port, wherein the port is selectively openable to provide access to the inflation tube, and a second port, wherein the second port is selectively openable to provide access to the cannula.

15. The medical ventilation device according to claim 1, further comprising a heat and moisture exchange filter.

16. A medical ventilation system comprising:
    a tracheal tube comprising a cannula having proximal and distal ends, wherein the tracheal tube is in fluid communication with an inspiratory pressure source adapted to provide respiratory gases to a patient at an inspiratory pressure;
    an inflatable cuff adapted to be inflated to the inspiratory pressure, the cuff attached to and surrounding a portion of the cannula toward the distal end thereof;
    an inspiratory pressure inflation tube having first and second ends, the first end in communication with an interior of the inflatable cuff, the second end adapted to communicate with the inspiratory pressure source and a cuff pressure monitoring device;
a pressure valve in communication with the inspiratory pressure inflation tube; and
a ventilator, wherein the second end of the inflation tube is in communication with the ventilator and the ventilator is adapted to inflate the cuff to the inspiratory pressure.

17. The medical ventilation system according to claim 16, further comprising a monitoring device operably attached to the tracheal tube.

18. The medical ventilation system according to claim 16, further comprising an electronic cuff pressure regulator operably attached to the tracheal tube.

19. The medical ventilation system according to claim 16, further comprising an anesthesia gas monitoring unit operably attached to the tracheal tube.

20. The medical ventilation system according to claim 16, further comprising a heat and moisture exchange filter between the ventilator and inflation tube.

* * * * *